United States Patent
Tierney et al.

[11] 4,019,374
[45] Apr. 26, 1977

[54] ELECTROMAGNETIC IMPULSER FOR DYNAMICALLY LOADING A STRUCTURE

[75] Inventors: William S. Tierney, Palos Verdes Peninsula; James E. Wright, Long Beach, both of Calif.

[73] Assignee: TRW Inc., Redondo Beach, Calif.

[22] Filed: July 24, 1975

[21] Appl. No.: 598,900

[52] U.S. Cl. .............................................. 73/71.5 R
[51] Int. Cl.² ........................................ B06B 1/04
[58] Field of Search ................... 73/71.5 R, 67, 12; 317/124; 335/17, 298, 219; 336/45

[56] References Cited
UNITED STATES PATENTS

| | | | |
|---|---|---|---|
| 2,412,240 | 12/1946 | Williams et al. | 73/67 |
| 3,522,460 | 8/1970 | Spurlin | 73/71.5 R |
| 3,641,811 | 2/1972 | Gnaedinger et al. | 73/71.5 R |
| 3,795,286 | 3/1974 | Meyer | 73/71.5 R |

*Primary Examiner*—Richard C. Queisser
*Assistant Examiner*—Stephen A. Kreitman
*Attorney, Agent, or Firm*—John J. Connors; Benjamin DeWitt; Donald R. Nyhagen

[57] ABSTRACT

An impulser for percussively loading a structure to generate stress waves in the structure by driving a hammer into impact relation with the structure and generating an electrical signal in timed relation to the impact. The impulser may embody means, such as suction cups, for firmly attaching the impulser to the structure and an anvil which is interposed between the hammer and structure and spring loaded against the structure for transmitting the hammer impact to the structure without damaging the structure.

1 Claim, 2 Drawing Figures

ELECTROMAGNETIC IMPULSER FOR DYNAMICALLY LOADING A STRUCTURE

RELATED APPLICATIONS

Reference is made to copending applications Ser. No. 456,998 by Pravin G. Bhuta et al. for "Optical Signature Method and Apparatus for Structural Integrity Verification", Ser. No. 598,901 by Jerold L. Jacoby et al. for "Optical Signature Instrument For Structural Integrity Verification", and Ser. No. 598,897 by Jerold L. Jacoby et al. for "Universal Holographic Optics Orientation Assembly".

BACKGROUND OF THE INVENTION

1. Field

This invention relates generally to percussive devices and more particularly to a novel impulser for percussively loading a structure to generate stress waves in the structure.

2. Prior Art

As will appear from the ensuing description, the impulser of the present invention may be used for a variety of purposes. The principal application of the impulser, however, is in the holographic instrument described in the above mentioned copending application Ser. No. 598,901. The latter application describes a holographic instrument which may be used as an optical signature instrument to determine the structural integrity of a structure, such as an aircraft, by percussively loading the structure to generate stress waves in the structure and recording two successive holograms of the structure on the same holographic recording medium in timed relation to propagation of the stress waves through the structure. These stress waves produce varying stress conditions in the structure with the result that the two successive holograms are recorded under different stress conditions in the structure. Accordingly, the resulting double exposure hologram constitutes a holographic interferrogram containing a deformation fringe pattern representing the deformational displacements produced in the structure by the change in stress conditions between the two holograms.

As described in the application, interferrograms produced in this way at different times but under the same stress conditions may be compared to evaluate the structural integrity of the structure by determining changes, if any, in the interferrogram fringe patterns. Such fringe pattern changes are indicative of changes in the structural integrity due to fatigue damage, stress corrosion cracking, and other causes.

Satisfactory operation of the optical signature instrument requires percussive loading of the structure with the same force each time the structure is inspected and recording of the two holograms during each inspection in precise timed relation to application of the percussive load. In some applications, the structure being inspected must be protected against damage by the percussive loading means.

SUMMARY

This invention provides an impulser which is particularly adapted for use in the holographic instrument described above to percussively load the structure to be inspected and thereby generate in the structure the stress waves required for operation of the instrument. The impulser will be described in the context of this use but is capable of other uses, as will become readily evident from the ensuing description.

The impulser has a frame mounting means, such as suction cups, for securing the frame firmly to the structure to be inspected. Supported on this frame for movement into frame inpact or percussive relation to the structure is a hammer which is driven through its impact or percussion stroke by hammer driving means on the frame. In the particular impulser embodiment described, this hammer is the plunger of a solenoid and is driven through its percussion stroke by electromagnetic action.

In order to protect the structure being inspected against damage by the impulser hammer or plunger, an anvil is interposed between the structure and the hammer. This anvil is spring loaded against the structure. The hammer strikes the anvil to transmit the impact to the structure without damage to the structure.

The impulser is also equipped with means for generating an electrical signal in timed relation to the impact for triggering the laser of the optical signature instrument. In the particular embodiment described, this signal generating means comprises a light source and photodetector which are uncovered by an adjustable timing shaft on the impulser plunger during its percussion stroke to permit light transmission from the source to the detector.

DESCRIPTION OF THE PREFERRED EMBODIMENT

Figure 1:
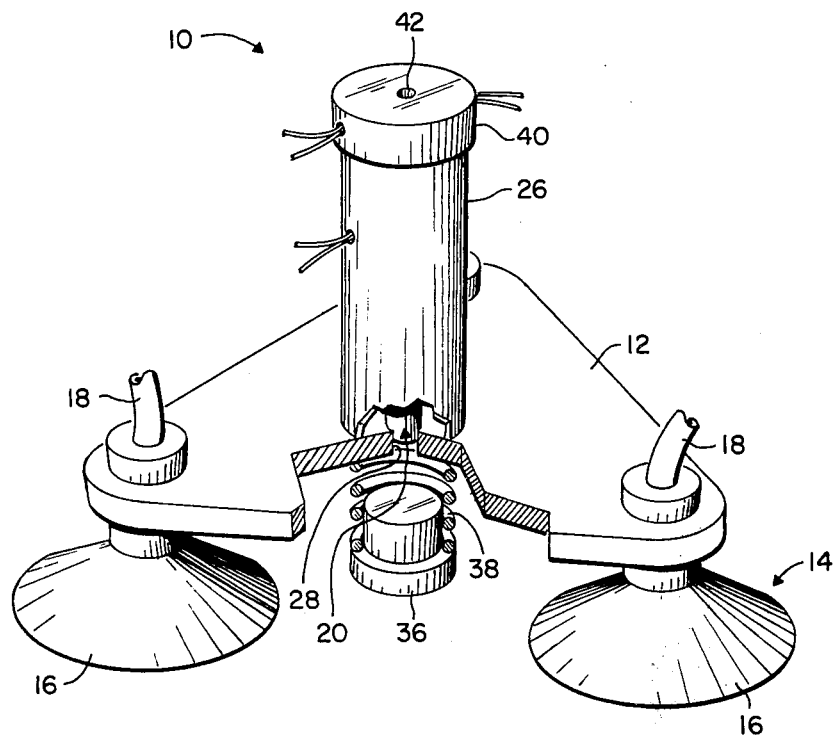
FIG. 1 is a perspective view of an impulser according to the invention.

Turning to the drawings, the illustrated impulser 10 comprises a frame 12 in the form of a generally triangular plate mounting means 14 for firmly attaching the frame to a sturcture to be inspected by the optical signature instrument discussed earlier or other object to be percussively loaded. The illustrated attaching means 14 comprise suction cups 16 for seating against the structure, and tubes 18 through which the cups may be evacuated to clamp the cups to the structure.

Figure 2:
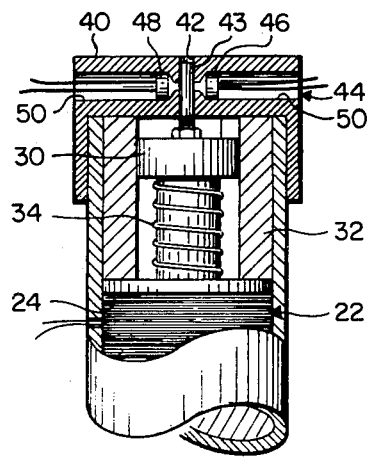
FIG. 2 is a fragmentary cross-section through the upper end of the impulser.

Supported on the frame 12 for movement into and from impact or percussion relation to the structure is a hammer 20 and means 22 for driving the hammer through its percussion and return strokes. In the embodiment shown, the hammer 20 is the plunger of a solenoid which forms the plunger driving means 22. The coil 24 of this solenoid is contained in a sleeve housing 26, the lower end of which is firmly secured to the frame plate 12. The lower end of plunger 20 extends slidably through a bore 28 in the plate 12. On the upper end of the plunger is a shoulder 30 which slides in a sleeve 32 in the upper end of sleeve 26. A spring 34 acting against this shoulder urges the plunger upwardly to its normal retracted position of FIGS. 1 and 2. Energizing of the coil 24 extends the plunger downwardly into impact with an anvil 36 below the frame plate 12. This anvil is attached to the plate by a spring 37. The upper end of sleeve 26 is closed by a cylinder cap 40 having an opening 42 which receives an adjustable timing shaft 43 threaded in the plunger 20.

Impulser 10 is equipped with means 44 for generating a signal in response to extension of the plunger 20 by energizing of the coil 24. The signal generating means show comprises a light-emitting diode 46 and a photodiode detector 48 mounted in coaxial diametrically opposed bores 50 intersecting the cap opening 42. When the plunger 10 is retracted, its timing shaft 43 blocks the bores to block light transmission from the diode to the detector. Extension of the plunger uncovers the bores to permit light transmission to the detector which then generates an output signal.

In use, the impulser 10 is placed on the structure or other object to be percussively loaded and the suction cups 16 are evacuated to firmly clamp the impulser frame 12 to the structure. The anvil 36 is thereby firmly clamped between the structure and frame 12. The impulser solenoid coil 24 is then energized to drive the plunger or hammer 20 downwardly against the anvil to transmit an impact through the anvil into the structure without damaging the structure.

When the plunger 20 decends or extends through its percussion stroke, its timing shaft 32 uncovers the sleeve bores 50, thereby causing the detector 48 to generate an output signal. In use of the impulser in the optical signature instrument of copending application Ser. No. 598,901 the impulser solenoid is energized from the instrument shutter and the signal from the impulser triggers the instrument laser, as described in the application. The timing shaft is adjustable to vary the timing of the impulser signal relative to the impact produced by the impulser and is fixed in position by the illustrated jam nut.

What is claimed is:

1. An impulser for percussively loading a structure comprising:

a plate;

suction cups secured to one side of said plate including means through which said cups may be evacuated to firmly attach said plate to said structure;

a solenoid mounted on the other side of said plate on a transverse axis of the plate; an anvil at said one side of said plate on the axis of said solenoid for seating against said structure;

a compression spring securing said anvil to said plate;

a plunger movable in said solenoid from a normal retracted position through a percussion stroke toward said anvil by electromagnetic action to impact one end of said plunger against said anvil and thereby deliver an impulse to said structure;

a spring for urging said plunger to its retracted position;

signal generating means including an axially adjustable timing shaft threaded axially in the other end of said plunger, a light source and a photodetector situated at diametrically opposite sides of said timing shaft in a manner such that said shaft blocks light transmission from said source to said detector in said normal retracted position of said plunger and said timing shaft moves through said percussion, stroke with said plunger and from between said light source and detector to permit light transmission to said detector, whereby the detector generates an electrical signal in timed relation to said impulse; and said timing shaft is adjustable relative to said plunger in the axial direction of said plunger.

* * * * *